(12) United States Patent
Yonehara

(10) Patent No.: US 10,989,714 B2
(45) Date of Patent: Apr. 27, 2021

(54) MEASUREMENT OF GLYCOPROTEIN

(71) Applicant: ARKRAY, Inc., Kyoto (JP)

(72) Inventor: Satoshi Yonehara, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 236 days.

(21) Appl. No.: 16/148,889

(22) Filed: Oct. 1, 2018

(65) Prior Publication Data

US 2019/0137502 A1    May 9, 2019

(30) Foreign Application Priority Data

Oct. 2, 2017 (JP) .............. JP2017-192863
Sep. 28, 2018 (JP) .............. JP2018-185124

(51) Int. Cl.

| | |
|---|---|
| *C12Q 1/26* | (2006.01) |
| *G01N 33/52* | (2006.01) |
| *G01N 33/58* | (2006.01) |
| *G01N 33/68* | (2006.01) |
| *G01N 33/72* | (2006.01) |
| *C07K 14/47* | (2006.01) |
| *C07K 14/76* | (2006.01) |
| *C07K 14/805* | (2006.01) |

(52) U.S. Cl.
CPC ......... *G01N 33/581* (2013.01); *C07K 14/473* (2013.01); *C07K 14/76* (2013.01); *C07K 14/805* (2013.01); *C12Q 1/26* (2013.01); *G01N 33/52* (2013.01); *G01N 33/6803* (2013.01); *G01N 33/6893* (2013.01); *G01N 33/723* (2013.01); *G01N 2333/4728* (2013.01); *G01N 2800/042* (2013.01)

(58) Field of Classification Search
CPC ............. G01N 33/581; G01N 33/6803; G01N 33/723; G01N 33/52; G01N 33/6893; G01N 2333/4728; G01N 2800/042; G01N 21/78; G01N 33/68; C12Q 1/26; C07K 14/473; C07K 14/76; C07K 14/805
See application file for complete search history.

(56) References Cited

U.S. PATENT DOCUMENTS

| | | |
|---|---|---|
| 5,370,990 A | 12/1994 | Staniford et al. |
| 2003/0157593 A1 | 8/2003 | Kurosawa et al. |
| 2003/0186449 A1* | 10/2003 | Yonehara ............... G01N 21/31 436/66 |
| 2004/0157285 A1 | 8/2004 | Ishimaru et al. |
| 2005/0101771 A1 | 5/2005 | Kouzuma et al. |

(Continued)

FOREIGN PATENT DOCUMENTS

| | | |
|---|---|---|
| EP | 1726660 A1 | 11/2006 |
| EP | 2639586 A1 | 9/2013 |

(Continued)

OTHER PUBLICATIONS

Extended European Search Report issued in corresponding European Patent Application No. 18198185.3 dated Dec. 14, 2018.

(Continued)

*Primary Examiner* — Jennifer Wecker
*Assistant Examiner* — Michael Paul Shimek
(74) *Attorney, Agent, or Firm* — Morgan, Lewis & Bockius LLP

(57) ABSTRACT

Provided is a method for measuring a glycoprotein using an enzymatic method, and the method includes simplified steps.

19 Claims, 1 Drawing Sheet

(56) References Cited

U.S. PATENT DOCUMENTS

| | | | |
|---|---|---|---|
| 2009/0081718 A1 | 3/2009 | Yonehara et al. | |
| 2011/0250627 A1 | 10/2011 | Yuan et al. | |
| 2016/0123999 A1 | 5/2016 | Ogawa et al. | |
| 2016/0251695 A1 | 9/2016 | Masakari et al. | |
| 2017/0355967 A1 | 12/2017 | Masakari et al. | |

FOREIGN PATENT DOCUMENTS

| | | | | |
|---|---|---|---|---|
| EP | 3061819 A1 | 8/2016 | | |
| JP | 3034698 B2 | 2/2000 | | |
| JP | 2008-295305 A | 12/2008 | | |
| JP | 4231668 B2 | 3/2009 | | |
| JP | 2009-072136 A | 4/2009 | | |
| JP | 4341809 B2 | 10/2009 | | |
| JP | 5878096 B2 | 3/2016 | | |
| WO | 03/029229 A1 | 4/2003 | | |
| WO | 2006/120976 A1 | 11/2006 | | |
| WO | 2008/013874 A1 | 1/2008 | | |
| WO | 2015/005257 A1 | 1/2015 | | |
| WO | 2015/060429 A1 | 4/2015 | | |
| WO | 2016/063984 A1 | 4/2016 | | |
| WO | WO-2016063984 A1 * | 4/2016 | .............. | C12M 1/40 |

OTHER PUBLICATIONS

Office Action issued in corresponding European Patent Application No. 18198185.3 dated Feb. 5, 2021.

* cited by examiner

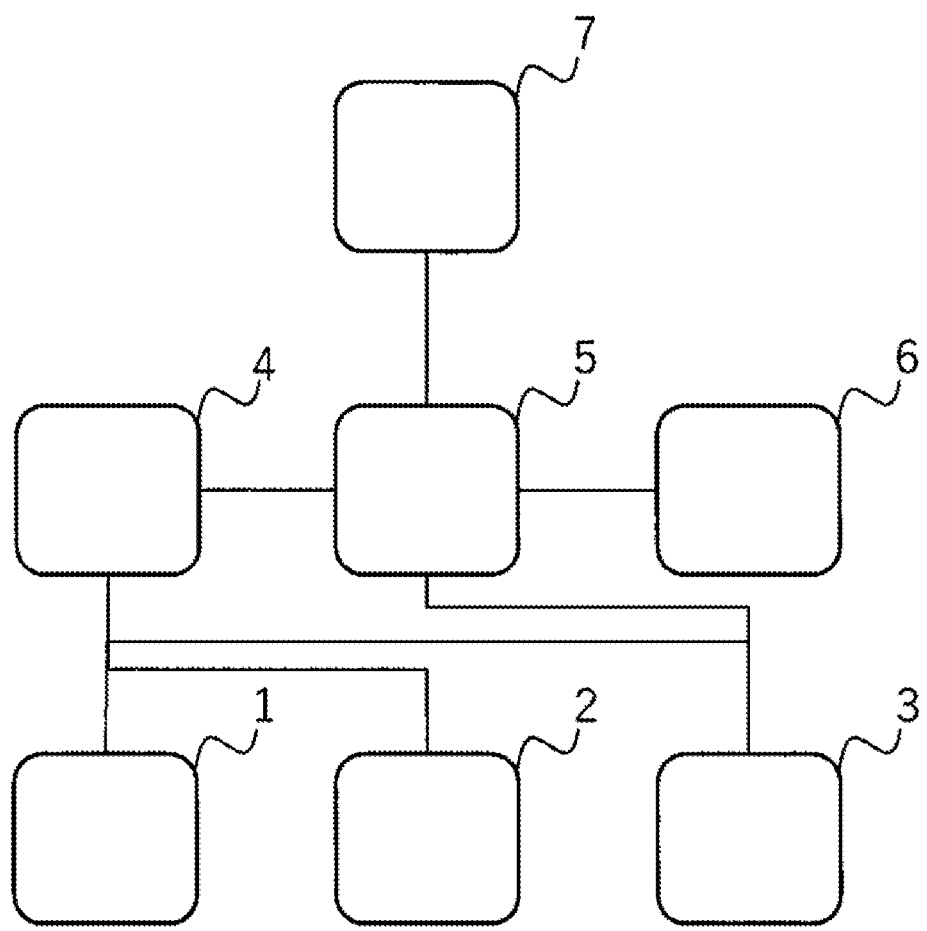

MEASUREMENT OF GLYCOPROTEIN

BACKGROUND OF THE INVENTION

1. Field of the Invention

The present disclosure relates to measurement of a glycoprotein, and more specifically relates to a method for measuring a glycoprotein using an amadoriase, an apparatus for measuring a glycoprotein using an amadoriase, and a system for measuring a glycoprotein using an amadoriase.

2. Description of Related Art

An amadori compound is formed due to the coexistence of a protein and a sugar such as glucose, and therefore, the sugar level can be determined by measuring the amadori compound level. The sugar levels in human or animal blood, food, and the like can be measured.

In particular, measuring a glycoprotein level is important in the diagnosis and treatment of diabetes. Examples of a method for measuring a glycoprotein level include a method for measuring only a glycoprotein level, and a method for measuring a glycoprotein level and a protein level and calculating the ratio therebetween. A target protein may not be particularly limited, may be limited to a specific protein, or may be limited to a specific site of a specific protein.

In such measurement of a glycoprotein level, the fructosamine level, the glycoalbumin level, the glycohemoglobin level, the hemoglobin A1c level, or the like is measured.

For example, in the case of fructosamine, the glycation level of a protein or albumin in serum or plasma is measured, and in the case of glycoalbumin, the ratio between the glycation level of albumin in serum or plasma and the albumin level is measured. In the case of glycohemoglobin, the glycation level of hemoglobin in blood is measured, or a ratio between the glycation level of hemoglobin and the hemoglobin level is measured. In the case of hemoglobin A1c, the glycation level (HbA1c level) of the N-terminus of the β-chain of hemoglobin in blood is measured, or a ratio between the HbA1c level and the hemoglobin level is measured.

In general, these glycoproteins are measured using an enzymatic method in which an amadoriase, which reacts with a glycoamino acid and a glycopeptide, is used.

A method for measuring fructosamine is disclosed in Japanese Patent No. 3034698, a method for measuring glycoalbumin is disclosed in Japanese Patent No. 4341809 and JP 2008-295305A, and a method for measuring only the glycohemoglobin level is disclosed in Japanese Patent No. 5878096 and the like.

In particular, measuring the glycohemoglobin ratio is important in the diagnosis and treatment of diabetes. Hemoglobin A1c (HbA1c), which is one type of glycohemoglobin, is particularly widely measured.

A method for measuring the glycohemoglobin level and the hemoglobin level is widely used to measure the glycohemoglobin ratio.

In general, the glycohemoglobin level is measured using an enzymatic method in which an amadoriase, which reacts with a glycoamino acid and a glycopeptide, is used. Examples of the amadoriase include a fructosyl peptide oxidase (Japanese Patent No. 4231668), which produces hydrogen peroxide and the like, and a fructosyl peptide dehydrogenase (WO 2016-63984), which has enhanced dehydrogenase activity.

An amadoriase used in a conventional enzymatic method has specificity for substrates ranging from a glycoamino acid to a glycopeptide. Therefore, when the glycohemoglobin level is measured using an amadoriase, glycohemoglobin needs to be treated with a protease or the like in advance and thus decomposed to glycoamino acids or glycopeptides for the purpose of facilitating the action of amadoriase (WO 2006-120976). When a protease is used to decompose glycohemoglobin, an amadoriase to be used in the measurement needs to be prepared as a separate reagent so as not to be decomposed by the protease.

On the other hand, it is difficult to measure the hemoglobin level after mixing a sample, an amadoriase, and a protease together because the color tone of Hb may change due to Hb reacting with the reagent (particularly the protease), and an overlap between the color tone of a color forming dye produced by the action of amadoriase depending on the glycohemoglobin concentration and the color tone of Hb affects the glycohemoglobin value.

At present, reagents used in a two-reagent system or reagents used in a three-reagent system are used as reagents for measurement of the glycohemoglobin level using an enzymatic method. Examples of the reagent configuration of the two-reagent system include configurations 1 to 4 below.

Configuration 1
First agent: amadoriase, buffer
Second agent: protease, color forming agent, buffer
Configuration 2
First agent: protease, buffer
Second agent: amadoriase, color forming agent, buffer
Configuration 3
First agent: amadoriase, color forming agent, buffer
Second agent: protease, buffer
Configuration 4
First agent: protease, color forming agent, buffer
Second agent: amadoriase, buffer Recent improvements in an amadoriase have led to the discovery of an amadoriase (also referred to as "glycoprotein-directed amadoriase" hereinafter) that has substrate specificity for a glycoprotein (i.e., acts directly on a glycoprotein) (WO 2015-005257 and WO 2015-060429). For example, a measurement method that includes performing steps (i) and (ii) below sequentially is disclosed as a method for measuring the glycohemoglobin level using a glycoprotein-directed amadoriase.

(i) Step of allowing a glycoprotein-directed amadoriase to act on glycohemoglobin in a sample and thereby oxidizing the glycohemoglobin.

(ii) Step of measuring substances produced or consumed in step (i) above.

It should be noted that the hemoglobin level is measured using a method for measuring the red color of a heme of hemoglobin. The types of hemoglobin include an oxidized form and a reduced form. The charged state varies depending on the types of hemoglobin, and the spectrum thus varies. Therefore, it is necessary to use a denaturant to change the type of hemoglobin to a specific type.

SUMMARY OF THE INVENTION

When a glycoprotein ratio is measured using two-reagent system reagents for the enzymatic method, steps of adding two solutions sequentially are performed. Specifically, two steps, namely a step of mixing a sample and a first agent together and a step of mixing a second agent with the obtained mixture, are performed. Accordingly, the method for measuring a glycoprotein ratio using reagents of a two-reagent system includes complicated steps. Moreover, it takes time to perform operations such as dispensing and mixing due to the two steps being performed, thus making it difficult to save time.

In one aspect, the present disclosure provides a method for measuring a glycoprotein using an enzymatic method, and the method includes simplified steps.

In one aspect, the present disclosure relates to a method for measuring a glycoprotein in a sample, the method including (1) to (3) below, wherein the reagent mixed with a sample in order to perform (2) and (3) below is a single reagent. Hereinafter, this measurement method is also referred to as "measurement method according to the present disclosure", and the reagent that is mixed with the sample in order to perform (2) and (3) below is also referred to as the "reagent of a single-reagent system" or "a single-reagent system reagent". It should be noted that the reagent of a single-reagent system may be a reagent that is mixed with a sample in order to perform (1) to (3) below in the present disclosure.

(1) Denaturing a protein in the sample.
(2) Reacting a glycoprotein in the sample with an amadoriase to allow a color forming agent to produce a color.
(3) Measuring the developed color signal of the sample after (1) and (2), and calculating the glycoprotein level.

In another aspect, the present disclosure relates to an apparatus or system for measuring a glycoprotein configured to perform the measurement method according to the present disclosure.

With the present disclosure, the steps included in a method for measuring a glycoprotein using an enzymatic method can be simplified, for example. With the present disclosure, a step of adding two or three reagents to a hemolyzed sample can be changed into a step of mixing a single reagent thereto, for example. This makes it possible to save time when measuring the hemoglobin A1c ratio (HbA1c %), for example. Moreover, since a single reagent is mixed, both the glycohemoglobin level and the hemoglobin level can be measured in the same solution, for example, thus making it possible to improve the accuracy and precision of the measurement.

BRIEF DESCRIPTION OF THE DRAWINGS

FIG. 1 is an explanatory diagram of an example of an apparatus or system for measuring a glycoprotein in which a measurement method according to the present disclosure is executed.

DESCRIPTION OF THE INVENTION

The "measurement of a glycoprotein" as used herein may encompass measuring a glycoprotein level in one embodiment, measuring a glycoprotein level and a protein level in another embodiment, and measuring a glycoprotein level and a protein level to determine the ratio therebetween in yet another embodiment.

The term "protein" as used herein may encompass "glycoprotein" unless otherwise stated.

The term "mixing the reagent of a single-reagent system and a sample" as used herein encompasses adding the single-reagent system reagent to a sample, and adding a sample to the single-reagent system reagent.

With the measurement method according to the present disclosure, in one or more embodiments, mixing a sample and the reagent of a single-reagent system only once makes it possible, in a single vessel (e.g., photometric cell), to denature a protein, react a glycoprotein with an amadoriase, allow a color forming agent to produce a color, measure the developed color signal of the color forming agent, and optionally measure the developed color signal of the denatured protein.

The term "denaturing a protein in a sample using the reagent of a single-reagent system" as used herein means that the reagent of a single-reagent system includes a denaturant (or a substance with denaturing activity) that can denature a protein in a sample. As described later, a sample prior to mixing may contain a surfactant (denaturant) for hemolysis or the like.

Examples of the glycoprotein measured using the measurement method according to the present disclosure include fructosamine, glycoalbumin, and glycohemoglobin. In one embodiment, glycoalbumin or glycohemoglobin is measured. An example of the glycohemoglobin is hemoglobin A1c (HbA1c), which is Hb in which the N-terminus of the β-chain is glycated.

As a measurement sample according to the present disclosure, a sample containing a glycoprotein can be used. When the glycoprotein is glycohemoglobin, the measurement sample includes a sample containing hemoglobin and glycohemoglobin. In one or more non-limiting embodiments, examples of the measurement sample include samples containing erythrocytes, such as whole blood and hemocytes, and samples obtained by subjecting such samples to hemolysis. When the measurement sample contains erythrocytes, the sample may be hemolyzed using the reagent of a single-reagent system or a means other than the reagent of a single-reagent system to produce a hemolyzed sample. Erythrocytes can be hemolyzed using existing methods. Examples of the hemolysis methods include a method employing osmotic pressure (e.g., water), a method employing a surfactant, and a method employing ultrasonic waves. Using a substance with denaturing activity such as a surfactant enables both hemolysis and the denaturation of a protein.

In one or more embodiments, the calculating the glycoprotein level such as the HbA1c level and the protein level such as the hemoglobin level from the developed color signal of the sample may be performed by a known method.

Accordingly, in one aspect, the present disclosure relates to a method for measuring glycohemoglobin in a sample, the method including (1) to (4) below, wherein a reagent mixed with a sample in order to perform (1) to (4) below is a single reagent.

(1) Denaturing hemoglobin in the sample.
(2) Reacting glycohemoglobin in the sample with an amadoriase to allow a color forming agent to produce a color.
(3) Measuring the developed color signal of the sample after (1) and (2), and calculating the glycohemoglobin level.
(4) Measuring the developed color signal of the sample after (1) and (2), and calculating the hemoglobin level.

When the measurement sample is a sample containing erythrocytes, a means other than the reagent of a single-reagent system may be used to perform hemolysis and the denaturation of hemoglobin. Specifically, in one aspect, the present disclosure relates to a method for measuring glycohemoglobin in a sample, the method including (0) to (4) below, wherein a reagent mixed with a sample in order to perform (2) to (4) below is a single reagent.

(0) Hemolyzing erythrocytes in the sample to release hemoglobin from the erythrocytes.

(1) Denaturing hemoglobin in the sample.

(2) Reacting glycohemoglobin in the sample with an amadoriase to allow a color forming agent to produce a color.

(3) Measuring the developed color signal of the sample after (1) and (2), and calculating the glycohemoglobin level.

(4) Measuring the developed color signal of the sample after (1) and (2), and calculating the hemoglobin level.

Embodiment Employing Glycoprotein-Directed Amadoriase

In one embodiment, an amadoriase (glycoprotein-directed amadoriase) that has substrate specificity for a glycoprotein (i.e., acts directly on a glycoprotein) is used as the amadoriase in the measurement method according to the present disclosure.

The "glycoprotein-directed amadoriase" as used herein refers to an amadoriase that can recognize the glycated moiety of a glycoprotein as a substrate and react with the glycoprotein even when the glycoprotein has not been decomposed to peptides using a protease or the like.

Examples of the glycoprotein-directed amadoriase include a glycoprotein-directed fructosyl peptide oxidase (direct FPDX), and a glycoprotein-directed fructosyl peptide dehydrogenase (direct FPDH) (WO 2015-005257 and WO 2015-060429).

Embodiment a Employing Direct FPDX

In non-limiting Embodiment A, the measurement method according to the present disclosure is a method for measuring a glycoprotein including (1) to (4) below, the method including mixing a single reagent (reagent of a single-reagent system) with a sample in order to perform (1) to (4) below or (2) to (4) below.

(1) Denaturing a protein in the sample.

(2) Reacting a glycoprotein in the sample with a direct FPDX to produce hydrogen peroxide.

(3) Reacting the produced hydrogen peroxide with a peroxidase (POD) to allow an oxidative color forming agent to produce a color.

(4) Measuring the developed color signal of the oxidative color forming agent that has produced a color, and calculating the glycoprotein level.

In one or more non-limiting embodiments, examples of the configuration of the reagent of a single-reagent system of Embodiment A include configurations A1 to A3 containing ingredients below as a single reagent. It should be noted that the reagent according to the present disclosure is not limited to those of the embodiments. The reagent of a single-reagent system may further contain another component.

Configuration A1: buffer, denaturant, direct FPDX, POD, oxidative color forming agent Configuration A2: buffer, direct FPDX, POD, oxidative color forming agent Configuration A3: buffer, direct FPDX, POD, leuco dye, compound represented by Formula (I) below:

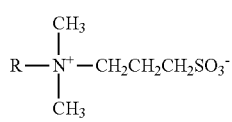

(I)

where R represents a hydrocarbon group having 8 to 17 carbon atoms.

As the buffer of Embodiment A, a buffer whose pH can be adjusted to near a neutral pH and that does not impair the reaction system can be used. Non-limiting examples of the buffer include N,N-bis(2-hydroxyethyl)-2-aminoethanesulfonic acid (BES), 3-morpholinopropanesulfonic acid (MOPS), N-tris(hydroxymethyl)methyl-2-aminoethanesulfonic acid (TES), 2-[4-(2-hydroxyethyl)-1-piperazinyl] ethanesulfonic acid (HEPES), N-[tris(hydroxymethyl) methyl]glycine (TRICINE), piperazine-1,4-bis(2-ethanesulfonic acid) (PIPES), piperazine-1,4-bis(2-hydroxy-3-propanesulfonic acid)dehydrate (POPSO), carbonic acid, phosphoric acid, boric acid, glycine, alanine, leucine, arginine, lysine, histidine, taurine, aspartic acid, asparagine, hydroxyproline, proline, threonine, serine, glutamic acid, glutamine, valine, cysteine, methionine, isoleucine, leucine, tyrosine, phenylalanine, ornithine, tryptophan, trishydroxymethylaminomethane, dimethylaminoethanol, triethanolamine, diethanolamine, monoethanolamine, N-methylaminoethanol, creatinine, imidazol, barbital, ammonia, ethylamine, diethylamine, and triethylamine.

As the peroxidase of Embodiment A, a peroxidase (POD) that can react with hydrogen peroxide and allow an oxidative color forming agent such as a leuco dye serving as a color forming substrate to emit light can be used. There is no particular limitation on the species from which the POD is derived. A non-limiting example of the POD is a horseradish peroxidase.

As the denaturant in configuration A1 of Embodiment A, a denaturant that can denature a protein and does not significantly impair the activity of an enzyme can be used. Non-limiting examples of the denaturant include denaturants (1) to (8) below. It should be noted that denaturants (1) to (7) may be used in combination with nitrous acid.

(1) 3-Lauryldimethylaminobutyric acid
(2) 3-Myristyldimethylaminobutyric acid
(3) Lauryldimethylaminopropanesulfonic acid
(4) Myristyldimethylaminopropanesulfonic acid
(5) Laurylamidepropyldimethylaminobutyric acid
(6) Myristamidepropyl betaine
(7) n-Dodecyl-@D-maltoside
(8) WST-3 (2-(4-iodophenyl)-3-(2,4-dinitrophenyl)-5-(2,4-disulfophenyl)-2H-tetrazolium)

When the glycohemoglobin level and the hemoglobin level are measured, a leuco dye is preferably used as the oxidative color forming agent in configurations A1 and A2 of Embodiment A.

Examples of the leuco dye include N-(carboxymethyl-aminocarbonyl)-4,4-bis(dimethylamino)biphenylamine (DA-64), 10-(carboxymethylaminocarbonyl)-3,7-bis(dimethylamino)phenothiazine (DA-67), 2,2'-aminobis(3-ethylbenzothiazolinone-6-sulfonic acid (ABTS), bis-(4-diethylaminophenyl)-2-sulfophenylmethane (BSPM), bis[3-bis(4-chlorophenyl)methyl-4-dimethylaminophenyl]amine (BCMA), 10-N-methylcarbamoyl-3,7-dimethylamino-10H-phenothiazine (MCDP), o-tolidine, 3,3'-diaminobenzidine.4HCl (DAB), 3-(4-hydroxyphenyl)propionic acid (HPPA), 3,3',5,5'-tetramethylbenzidine (TMBZ), N-(3-sulfopropyl)-3,3',5,5'-tetramethylbenzidine.Na (TMBZ-PS), and N,N',N',N'',N''-hexa(3-sulfopropyl)-4,4',4''-triaminotriphenylmethane.6Na (TPM-PS), which are easily obtained.

When fructosamine and glycoalbumin are measured, a Trinder's reagent that produces a pigment through oxidative condensation of a coupler such as 4-aminoantipyrine (4-AA) or 3-methyl-2-benzothiazolinone hydrazone and a chromogen such as phenol, or a leuco dye can be used as the oxidative color forming agent in configurations A1 and A2 of Embodiment A.

As a hydrogen donor for the Trinder's reagent, phenol derivatives, aniline derivatives, toluidine derivatives, and the like can be used. Specific examples thereof include sodium N-(3-sulfopropyl)aniline monohydrate (HALPS), sodium N-ethyl-N-(3-sulfopropyl)-3-methylaniline monohydrate (TOPS), sodium N-ethyl-N-(2-hydroxy-3-sulfopropyl)-3,5-dimethoxyaniline monohydrate (MAOS), sodium N-(3-sulfopropyl)-3,5-dimethoxyaniline monohydrate (MAPS), sodium N-(2-hydroxy-3-sulfopropyl)-3,5-dimethoxyaniline (HDAOS), sodium N-ethyl-N-(3-sulfopropyl)-3,5-dimethoxyaniline monohydrate (DAPS), sodium N-ethyl-N-(2-hydroxy-3-sulfopropyl)-3,5-dimethoxyaniline (DAOS), sodium N-ethyl-N-(3-sulfopropyl)aniline (ALPS), sodium N-ethyl-N-(3-sulfopropyl)-3-methoxyaniline monohydrate (ADPS), sodium N-ethyl-N-(2-hydroxy-3-sulfopropyl)-3-methoxyaniline dihydrate (ADOS), N-ethyl-N-(2-hydroxy-3-sulfopropyl)-m-toluidine (TOOS), and disodium N,N-bis(4-sulfobutyl)-3-methylaniline (TODB).

Configurations A1 and A2 of Embodiment A may further include a dyestabilizer such as a reductant or a surfactant.

Configuration A3 of Embodiment A includes the compound represented by Formula (I) that can exhibit two functions, namely those of a denaturant and a dye stabilizer. In Formula (I), R preferably has 8 to 17 carbon atoms, more preferably 12 to 16 carbon atoms, and even more preferably 14 carbon atoms, from the viewpoint that measurement using an enzymatic method is not inhibited and the stability of the leuco dye is enhanced. The hydrocarbon group represented by R is preferably an alkyl group, and more preferably a linear alkyl group, from the same viewpoint. R is preferably a dodecyl group or a tetradecyl group, and more preferably a tetradecyl group, from the same viewpoint.

As a measurement sample of Embodiment A, a sample containing hemoglobin and glycohemoglobin can be used. In one or more non-limiting embodiments, examples of the measurement sample include samples containing erythrocytes, such as whole blood and hemocytes, and samples obtained by subjecting such samples to hemolysis. When the measurement sample contains erythrocytes, the sample may be hemolyzed using the reagent of a single-reagent system or a means other than the reagent of a single-reagent system to produce a hemolyzed sample. Erythrocytes can be hemolyzed using the existing methods. Examples of the hemolysis methods include a method employing osmotic pressure (e.g., water), a method employing a surfactant, a freezing method, and a method employing ultrasonic waves.

In one or more other embodiments, the developed color signal of the present disclosure includes absorbance, reflectance, or transmittance.

In one or more embodiments, the calculation of the HbA1c level may include converting the developed color signal into the HbA1c level using predetermined conversion factor. The conversion of the developed color signal into the HbA1c level using the predetermined conversion factor may be performed by converting the developed color signal, such as absorbance, obtained by the measurement of HbA1c, into HbA1c level on the basis of one of the conversion rules (i) to (iv) below, in one or more embodiments. The conversion rules (iv) may be performed in combination with one or more the conversion rules (i) to (iii), in one or more embodiments.

(i) Creating a calibration curve by using a known calibrating substance in the sample, and converting absorbance derived from HbA1c into the HbA1c level by using the calibration curve;

(ii) Creating a calibration curve of the color forming agent as a calibrator (calibration standard), and converting absorbance of the color forming agent into the HbA1c level by using the calibration curve of the color forming agent;

(iii) Calculating a ratio of absorbance obtained at different wavelengths, and converting the ratio into HbA1c level by using a calibration curve of the absorbance ratio;

(iv) Calculating the amount of change in the absorbance by subtracting absorbance a from absorbance b and converting the amount of change in the absorbance into the HbA1c level by using the calibration curve for the amount of change in absorbance.

the absorbance a: absorbance immediately after mixing of the sample and the reagent the absorbance b: absorbance after a lapse of a predetermined time from the mixing of the sample and the reagent The known calibrating substance, in one or more embodiments, may include calibration standards containing known amounts of HbA1c. The calibration standard, in one or a plurality of embodiments, may include frozen whole blood or blood cells, Hb solution containing HbA1c obtained by purified them, or substance containing buffer solutions and/or stabilization of Hb agents and the like therein. The known calibrating substance, in one or more embodiments, may include a primary standard substance or a regular reference substance provided by a public institution, a proofreading substance attached to a kit, and the like.

In one or more embodiments of immediately after mixing, it may be about 5 seconds to 30 seconds after mixing of the sample and the reagent. In one or more embodiments of after a lapse of a predetermined time, it may be about 1 minute to 3 minutes after mixing of the sample and the reagent.

With the calculation of the HbA1c level, in one or more embodiments, even in a case where the developed color signal is the reflectance and the transmittance can be performed.

When the measurement target of Embodiment A is glycohemoglobin, an example of Embodiment Aa for measuring the glycohemoglobin ratio (ratio of the glycohemoglobin level to the hemoglobin level) is a method for measuring the glycohemoglobin ratio including (1) to (5) below, the method including mixing a single reagent (reagent of a single-reagent system) with a sample in order to perform (1) to (5) below.

Embodiment Aa (1) Denaturing hemoglobin in the sample.
(2) Reacting glycohemoglobin in the sample with a direct FPDX to produce hydrogen peroxide.
(3) Reacting the produced hydrogen peroxide with a peroxidase (POD) to allow a leuco dye to produce a color.
(4) measuring the developed color signal of the leuco dye that has produced a color, and calculating the glycohemoglobin level.
(5) Measuring the developed color signal of the denatured hemoglobin, and calculating the hemoglobin level.

When the measurement target of Embodiment A is glycohemoglobin, an example of Embodiment Ab for measuring the glycohemoglobin ratio (ratio of the glycohemoglobin level to the hemoglobin level) is a method for measuring the glycohemoglobin ratio including (0) to (5) below, the method including mixing a single reagent (reagent of a single-reagent system) with a sample in order to perform (2) to (5) below.

Embodiment Ab (0) Hemolyzing erythrocytes in the sample to release hemoglobin from the erythrocytes.
(1) Denaturing hemoglobin in the sample.
(2) Reacting glycohemoglobin in the sample with a direct FPDX to produce hydrogen peroxide.
(3) Reacting the produced hydrogen peroxide with a peroxidase (POD) to allow a leuco dye to produce a color.
(4) Measuring the developed color signal of the leuco dye that has produced a color, and calculating the glycohemoglobin level.
(5) Measuring the developed color signal of the denatured hemoglobin, and calculating the hemoglobin level.

Embodiments Aa and Ab may further include calculating the glycohemoglobin ratio from the glycohemoglobin level and the hemoglobin level.

In one or more embodiments, the glycohemoglobin of Embodiments Aa and Ab is hemoglobin A1c.

When the measurement target of Embodiment A is a glycoprotein (e.g., glycoalbumin) other than glycohemoglobin, and the glycoprotein ratio (ratio of the glycoprotein to the protein) is to be measured, the glycoprotein ratio can be determined from the glycoprotein level obtained through the measurement according to the present disclosure and the protein level obtained using another method in one or more embodiments. The glycohemoglobin ratio may also be determined in accordance with this procedure.

Examples of the method for determining the protein level include a biuret reaction method, a Lowry method in which a Folin phenol reagent is used, and a Bradford (Coomassie) method in which Coomassie G-250 is used. In the case of albumin, a BCG method and a BCP method can be used.

Freshly Prepared Form of Embodiment A

The reagent of a single-reagent system of Embodiment A need not take a single-reagent form, which contains pre-mixed ingredients (components) used for the measurement, from the viewpoint of the stability of the reagent. The reagent may be prepared fresh just before performing the measurement method according to the present disclosure. Non-limiting examples of the configuration of two reagents used to prepare the reagent of a single-reagent system in such embodiments include configurations A4 to A9 below. It should be noted that the reagent according to the present disclosure is not limited to those of the embodiments. The reagent may further contain another component.

Configuration A4
Reagent 1: buffer, denaturant, direct FPDX, POD
Reagent 2: buffer, oxidative color forming agent
Configuration A5
Reagent 1: buffer, direct FPDX, POD
Reagent 2: buffer, denaturant, oxidative color forming agent
Configuration A6
Reagent 1: buffer, POD
Reagent 2: buffer, denaturant, direct FPDX, oxidative color forming agent
Configuration A7
Reagent 1: buffer, denaturant, POD
Reagent 2: buffer, direct FPDX, oxidative color forming agent
Configuration A8
Reagent 1: buffer, direct FPDX, POD
Reagent 2: buffer, oxidative color forming agent
Configuration A9
Reagent 1: buffer, POD
Reagent 2: buffer, direct FPDX, oxidative color forming agent Configurations A4 to A9 of Embodiment A may further include a dye stabilizer such as a reductant or a surfactant. The buffer, denaturant, and oxidative color forming agent as described above can be used as those in configurations A4 to A9. The compound represented by Formula (I) may be used as the denaturant and/or dye stabilizer in configurations A4 to A9.

The term "freshly prepared form" as used herein refers to a form that includes preparing, for one or more samples, the reagent of a single-reagent system using a plurality of reagents immediately before performing the measurement method according to the present disclosure on one or more samples.

Embodiment B Employing Direct FPDH

In non-limiting Embodiment B, the measurement method according to the present disclosure is a method for measuring a glycoprotein including (1) to (3) below, the method including mixing a single reagent (reagent of a single-reagent system) with a sample in order to perform (1) to (3) below or (2) and (3) below.

(1) Denaturing a protein in the sample.
(2) Reacting a glycoprotein in the sample with a direct FPDH to allow a reductive color forming agent to produce a color.
(3) Calculating the glycoprotein level by measuring the developed color signal of the reductive color forming agent that has produced a color.

In one or more non-limiting embodiments, examples of the configuration of the reagent of a single-reagent system of Embodiment B include configurations B1 and B2 containing ingredients below as a single reagent. It should be noted that the reagent according to the present disclosure is not limited to those of the embodiments. The reagent of a single-reagent system may further contain another component.

Configuration B1: buffer, denaturant, direct FPDH, reductive color forming agent
Configuration B2: buffer, direct FPDH, reductive color forming agent The buffer, denaturant, and measurement sample of Embodiment B are the same as those of Embodiment A.

As the reductive color forming agent of Embodiment B, tetrazolium salts and the like can be used.

Examples of the tetrazolium salts include 2,5-diphenyl-3-(1-naphthyl)-2H-tetrazolium chloride (abbreviated as tetrazolium violet), 3,3'-(3,3'-dimethoxy-4,4'-biphenylene)-bis[2-(p-nitrophenyl)-5-phenyltetrazolium chloride] (abbreviated as nitroblue tetrazolium), 3,3'-(3,3'-dimethoxy-4,4'-biphenylene)-bis(2,5-diphenyltetrazolium chloride) (abbreviated as blue tetrazolium), 3-(4,5-dimethyl-2-thiazolyl)-2,5-diphenyltetrazolium bromide (abbreviated as MTT), 3-(p-iodophenyl)-2-(p-nitrophenyl)-5-phenyl-tetrazolium chloride, 2,2',5,5'-tetra-(p-nitrophenyl)-3,3'-(3-dimethoxy-4-diphenylene)-ditetrazolium chloride (abbreviated as nitroblue tetrazolium), 2,3,5-triphenyltetrazolium chloride, 3,3'-(3,3'-dimethoxy-4,4'-biphenylene)-bis-[2,5-bis(p-nitrophenyl)tetrazolium chloride], 3,3'-(4,4'-biphenylene)-bis(2,5-diphenyltetrazolium chloride), 2-(4-iodophenyl)-3-(4-nitrophenyl)-5-phenyl-2H-tetrazolium chloride (abbreviated as INT), 3,3'-[3,3'-dimethoxy-(1,1'-biphenyl)-4,4'-diyl]-bis[2-(4-nitrophenyl)-5-phenyl]-2H tetrazolium chloride (abbreviated as nitro-TB), 2-benzothiazoyl-3-(4-carboxy-2-methoxyphenyl)-5-[4-(2-sulfoethylcarbamoyl) phenyl]-2H-tetrazolium (abbreviated as WST-4), and 2,2'-dibenzothiazoyl-5,5'-bis[4-di(2-sulfoethyl) carbamoylphenyl]-3,3'-(3,3'-dimethoxy-4,4'-diphenylene) ditetrazolium disodium salt (abbreviated as WST-5).

Out of these tetrazolium salts, WST-4 and WST-5 are easy to prepare as a reagent due to their high solubility in water. In addition, WST-4 and WST-5 are characterized in that their absorption spectra include absorptions in a long wavelength region and are thus barely affected by the absorption spectra of a protein such as hemoglobin.

Configurations B1 and B2 of Embodiment B may further include a dye stabilizer. Examples of the dye stabilizer include sodium azide (WO2003/029229) and a pH adjuster (JP 2009-072136).

The measurement of the developed color signal and glycoprotein level of Embodiment B are the same as those of Embodiment A.

Configurations B1 and B2 of Embodiment B may include an electron transfer agent. Examples of the electro transfer agent include diaphorase, N-methylphenazine.methosulfates (e.g., N-methylphenazine.methosulfate, 1-methoxy-5-methylphenazine.methosulfate (1-methoxy PMS)), Meldola's blue, and methylene blue.

When the measurement target of Embodiment B is glycohemoglobin, an example of Embodiment Ba for measuring the glycohemoglobin ratio (ratio of the glycohemoglobin level to the hemoglobin level) is a method for measuring the glycohemoglobin ratio including (1) to (4) below, the method including mixing a single reagent (reagent of a single-reagent system) with a sample in order to perform (1) to (4) below.

Embodiment Ba (1) Denaturing hemoglobin in the sample.
(2) Reacting glycohemoglobin in the sample with a direct FPDH to allow a reductive color forming agent to produce a color.
(3) Measuring the developed color signal of the reductive color forming agent that has produced a color, and calculating the glycoprotein level.
(4) Measuring the developed color signal of the denatured hemoglobin, and calculating the hemoglobin level.

When the measurement target of Embodiment B is glycohemoglobin, an example of Embodiment Bb for measuring the glycohemoglobin ratio (ratio of the glycohemoglobin level to the hemoglobin level) is a method for measuring the glycohemoglobin ratio including (0) to (4) below, the method including mixing a single reagent (reagent of a single-reagent system) with a sample in order to perform (2) to (4) below.

Embodiment Bb (0) Hemolyzing erythrocytes in the sample to release hemoglobin from the erythrocytes.
(1) Denaturing hemoglobin in the sample.
(2) Reacting glycohemoglobin in the sample with a direct FPDH to allow a reductive color forming agent to produce a color.
(3) Measuring the developed color signal of the reductive color forming agent that has produced a color, and calculating the glycoprotein level.
(4) Measuring the developed color signal of the denatured hemoglobin, and calculating the hemoglobin level.

Embodiments Ba and Bb may further include calculating the glycohemoglobin ratio from the glycohemoglobin level and the hemoglobin level.

In one or more embodiments, the glycohemoglobin of Embodiments Ba and Bb is hemoglobin A1c.

When the measurement target of Embodiment B is a glycoprotein (e.g., glycoalbumin) other than glycohemoglobin, and the glycoprotein ratio (ratio of the glycoprotein to the protein) is to be measured, the glycoprotein ratio can be determined from the glycoprotein level obtained through the measurement according to the present disclosure and the protein level obtained using another method in one or more embodiments. The glycohemoglobin ratio may also be determined in accordance with this procedure. Examples of the method for determining the protein level include those described above.

Freshly Prepared Form of Embodiment B

The reagent of a single-reagent system of Embodiment B need not take a pre-mixed single-reagent form from the viewpoint of the stability of the reagent. The reagent may be prepared fresh just before performing the measurement method according to the present disclosure. Non-limiting examples of the configuration of two reagents used to prepare the reagent of a single-reagent system in such embodiments include configurations B3 and B4 below.

Configuration B3
Reagent 1: buffer, denaturant, direct FPDH
Reagent 2: buffer, reductive color forming agent
Configuration B4
Reagent 1: buffer, direct FPDH
Reagent 2: buffer, reductive color forming agent Configurations B3 and B4 of Embodiment B may further include the above-described dye stabilizer and/or electron transfer agent.

The buffer, denaturant, and oxidative color forming agent as described above can be used as those in configurations B3 and B4.

Embodiment Employing Amadoriase and Protease

In another embodiment, amadoriase that has substrate specificity for N-terminal glycated peptides and amino acids (also referred to simply as "glycopeptides" hereinafter) is used as the amadoriase in the measurement method according to the present disclosure. Examples of such amadoriase include a fructosyl peptide oxidase (FPDX) and a fructosyl peptide dehydrogenase (FPDH).

An enzyme that is active against glycoamino acids and/or glycopeptides and acts well on an amino acid that is lysine with a glycated ε amino group and/or a peptide in which an ε amino group is glycated can be used as the amadoriase used in the measurement of fructosamine or glycoalbumin. Examples thereof include oxidases derived from the genera *Gibberella*, *Aspergillus*, *Candida*, *Penicillium*, *Fusarium*, *Acremonium*, and *Debaryomyces*.

Embodiment C Employing FPDX

In non-limiting Embodiment C, the measurement method according to the present disclosure is a method for measuring a glycoprotein including (1) to (5) below, the method including mixing a single reagent (reagent of a single-reagent system) with a sample in order to perform (1) to (5) below or (2) to (5) below.

(1) Denaturing a protein in the sample.
(2) Reacting a glycoprotein in the sample with a protease to produce a glycopeptide.
(3) Reacting the glycopeptide with a FPDX to produce hydrogen peroxide.
(4) Reacting the produced hydrogen peroxide with a peroxidase to allow an oxidative color forming agent to produce a color.
(5) Calculating the glycoprotein level by measuring the developed color signal of the oxidative color forming agent that has produced a color.

In one or more non-limiting embodiments, examples of the configuration (constituents) of the reagent of a single-reagent system of Embodiment C include configurations C1 to C3 containing ingredients below as a single reagent. It should be noted that the reagent according to the present disclosure is not limited to those of the embodiments. The reagent of a single-reagent system may further contain another component.

Configuration C1: buffer, denaturant, protease, FPDX, POD, oxidative color forming agent
Configuration C2: buffer, protease, FPDX, POD, oxidative color forming agent
Configuration C3: buffer, protease, FPDX, POD, leuco dye, compound represented by Formula (I)

Configurations C1 to C3 of Embodiment C may further include the above-described dye stabilizer.

The buffer, denaturant, POD, oxidative color forming agent, leuco dye, compound represented by Formula (I), and measurement sample in configurations C1 to C3 are the same as those of Embodiment A.

As the protease of Embodiment C, a protease that is active at near a neutral pH and can react with glycohemoglobin to produce an N-terminal glycated peptide (including a glycoamino acid in the present disclosure) can be used. There is no particular limitation on the species from which the protease is derived and the enzyme family. Non-limiting examples of the protease include a serine protease, a threonine protease, a glutamic protease, an aspartic protease, and a metalloprotease.

Examples of the protease of Embodiment C include proteases derived from microorganisms belonging to the genera *Bacillus, Aspergillus, Streptomyces*, and the like. In addition, a serine protease is also preferable.

When the measurement target is glycoalbumin, a protease derived from a microorganism belonging to the genus *Bacillus* or *Streptomyces* is preferable due to its high activity against human albumin. Proteases derived from the genus *Bacillus*, such as subtilisin, nagarse, proteases type-VIII, -IX, -X, -XV, -XXIV, -XXVII, and -XXXI (these are manufactured by Sigma), and those such as thermolysin, Neutrase, Esperase, Savinase, Durazym, Biofeed Pro, Alcalase (these are manufactured by Novo Nordisk Bio Industry) are more preferable, and subtilisin, nagarse, protease type-XXVII, and the like are even more preferable.

The measurement of the developed color signal and glycoprotein level of Embodiment C are the same as those of Embodiment A.

When the measurement target of Embodiment C is glycohemoglobin, an example of Embodiment Ca for measuring the glycohemoglobin ratio (ratio of the glycohemoglobin level to the hemoglobin level) is a method for measuring the glycohemoglobin ratio including (1) to (6) below, the method including mixing a single reagent (reagent of a single-reagent system) with a sample in order to perform (1) to (6) below.

Embodiment Ca (1) Denaturing hemoglobin in the sample.
(2) Reacting glycohemoglobin in the sample with a protease to produce a glycopeptide.
(3) Reacting the glycopeptide with a FPDX to produce hydrogen peroxide.
(4) Reacting the produced hydrogen peroxide with a peroxidase to allow an oxidative color forming agent to produce a color.
(5) Measuring the developed color signal of the oxidative color forming agent that has produced a color, and calculating the glycoprotein level.
(6) Measuring the developed color signal of the denatured hemoglobin, and calculating the hemoglobin level.

When the measurement target of Embodiment C is glycohemoglobin, an example of Embodiment Cb for measuring the glycohemoglobin ratio (ratio of the glycohemoglobin level to the hemoglobin level) is a method for measuring the glycohemoglobin ratio including (0) to (6) below, the method including mixing a single reagent (reagent of a single-reagent system) with a sample in order to perform (2) to (6) below.

Embodiment Cb (0) Hemolyzing erythrocytes in the sample to release hemoglobin from the erythrocytes.
(1) Denaturing hemoglobin in the sample.
(2) Reacting glycohemoglobin in the sample with a protease to produce a glycopeptide.
(3) Reacting the glycopeptide with a FPDX to produce hydrogen peroxide.
(4) Reacting the produced hydrogen peroxide with a peroxidase to allow an oxidative color forming agent to produce a color.
(5) Measuring the developed color signal of the oxidative color forming agent that has produced a color, and calculating the glycoprotein level.
(6) Measuring the developed color signal of the denatured hemoglobin, and calculating the hemoglobin level.

Embodiments Ca and Cb may further include calculating the glycohemoglobin ratio from the glycohemoglobin level and the hemoglobin level.

In one or more embodiments, the glycohemoglobin of Embodiments Ca and Cb is hemoglobin A1c.

When the measurement target of Embodiment C is a glycoprotein (e.g., glycoalbumin) other than glycohemoglobin, and the glycoprotein ratio (ratio of the glycoprotein to the protein) is to be measured, the glycoprotein ratio can be determined from the glycoprotein level obtained through the measurement according to the present disclosure and the protein level obtained using another method in one or more embodiments. The glycohemoglobin ratio may also be determined in accordance with this procedure. Examples of the method for determining the protein level include those described above.

Freshly Prepared Form of Embodiment C

The reagent of a single-reagent system of Embodiment C need not take a pre-mixed single-reagent form from the viewpoint of the stability of the reagent. The reagent may be prepared fresh just before preparing the measurement method according to the present disclosure. Non-limiting examples of the configuration (constituents) of two reagents used to prepare the reagent of a single-reagent system in such embodiments include configurations C4 to C11 below.

Configuration C4
First reagent: buffer, denaturant, FPDX, POD
Second reagent: buffer, protease, oxidative color forming agent Configuration C5
First reagent: buffer, denaturant, protease, POD
Second reagent: buffer, FPDX, oxidative color forming agent Configuration C6
First reagent: buffer, denaturant, FPDX, oxidative color forming agent
Second reagent: buffer, protease, POD Configuration C7
First reagent: buffer, denaturant, protease, oxidative color forming agent
Second reagent: buffer, FPDX, POD Configuration C8
First reagent: buffer, FPDX, POD
Second reagent: buffer, protease, oxidative color forming agent Configuration C9
First reagent: buffer, protease, POD
Second reagent: buffer, FPDX, oxidative color forming agent Configuration C10
First reagent: buffer, FPDX, oxidative color forming agent
Second reagent: buffer, protease, POD Configuration C11
First reagent: buffer, protease, oxidative color forming agent
Second reagent: buffer, FPDX, POD Configurations C4 to C11 of Embodiment C may further include a dye stabilizer such as a reductant or a surfactant. The buffer, denaturant, oxidative color forming agent, and measurement sample in configurations C4 to C11 are the same as those of Embodiment A. The compound represented by Formula (I) may be used as the denaturant and/or dye stabilizer in configurations C4 to C11.

Embodiment D Employing FPDH

In non-limiting Embodiment D, the measurement method according to the present disclosure is a method for measuring a glycoprotein including (1) to (4) below, the method including mixing a single reagent (reagent of a single-reagent system) with a sample in order to perform (1) to (4) below or (2) and (4) below.

(1) Denaturing a protein in the sample.
(2) Reacting a glycoprotein in the sample with a protease to produce a glycopeptide.
(3) Reacting the glycopeptide with a FPDH to allow a reductive color forming agent to produce a color.
(4) Calculating the glycoprotein level by measuring the developed color signal of the reductive color forming agent that has produced a color.

In one or more non-limiting embodiments, examples of the configuration (constituents) of the reagent of a single-reagent system of Embodiment D include configurations D1 and D2 containing ingredients below as a single reagent. It should be noted that the reagent according to the present disclosure is not limited to those of the embodiments. The reagent of a single-reagent system may further contain another component.

Configuration D1
Reagent of single-reagent system: buffer, denaturant, protease, FPDH, reductive color forming agent Configuration D2
Reagent of single-reagent system: buffer, FPDH, reductive color forming agent Configurations D1 and D2 of Embodiment D may further include the above-described dye stabilizer and/or electron transfer agent.

The buffer, denaturant, reductive color forming agent, and measurement sample in configurations D1 and D2 are the same as those of Embodiment B, and the protease is the same as that of Embodiment C.

The measurement of the developed color signal and glycoprotein level of Embodiment D are the same as those of Embodiment A.

When the measurement target of Embodiment D is glycohemoglobin, an example of Embodiment Da for measuring the glycohemoglobin ratio (ratio of the glycohemoglobin level to the hemoglobin level) is a method for measuring the glycohemoglobin ratio including (1) to (5) below, the method including mixing a single reagent (reagent of a single-reagent system) with a sample in order to perform (1) to (5) below.

Embodiment Da (1) Denaturing hemoglobin in the sample.
(2) Reacting glycohemoglobin in the sample with a protease to produce a glycopeptide.
(3) Reacting the glycopeptide with a FPDH to allow a reductive color forming agent to produce a color.
(4) Measuring the developed color signal of the reductive color forming agent that has produced a color, and calculating glycoprotein level.
(5) Measuring the developed color signal of the denatured hemoglobin, and calculating the hemoglobin level.

When the measurement target of Embodiment D is glycohemoglobin, an example of Embodiment Db for measuring the glycohemoglobin ratio (ratio of the glycohemoglobin level to the hemoglobin level) is a method for measuring the glycohemoglobin ratio including (0) to (5) below, the method including mixing a single reagent (reagent of a single-reagent system) with a sample in order to perform (2) to (5) below.

Embodiment Db (0) Hemolyzing erythrocytes in the sample to release hemoglobin from the erythrocytes.
(1) Denaturing hemoglobin in the sample.
(2) Reacting glycohemoglobin in the sample with a protease to produce a glycopeptide.
(3) Reacting the glycopeptide with a FPDH to allow a reductive color forming agent to produce a color.
(4) Measuring the developed color signal of the reductive color forming agent that has produced a color, and calculating the glycoprotein level.
(5) Measuring the developed color signal of the oxidative color forming agent that has produced a color, and calculating the hemoglobin level.

Embodiments Da and Db may further include calculating the glycohemoglobin ratio from the glycohemoglobin level and the hemoglobin level.

In one or more embodiments, the glycohemoglobin of Embodiments Da and Db is hemoglobin A1c.

When the measurement target of Embodiment D is a glycoprotein (e.g., glycoalbumin) other than glycohemoglobin, and the glycoprotein ratio (ratio of the glycoprotein to the protein) is to be measured, the glycoprotein ratio can be determined from the glycoprotein level obtained through the measurement according to the present disclosure and the protein level obtained using another method in one or more embodiments. The glycohemoglobin ratio may also be determined in accordance with this procedure. Examples of the method for determining a protein level include those described above.

Freshly Prepared Form of Embodiment D

The reagent of a single-reagent system of Embodiment D need not take a pre-mixed single-reagent form from the viewpoint of the stability of the reagent. The reagent may be prepared fresh just before performing the measurement method according to the present disclosure. Non-limiting examples of the configuration of two reagents used to prepare the reagent of a single-reagent system in such embodiments include configurations D3 to D10 below.

Configuration D3
First reagent: buffer, denaturant, FPDH
Second reagent: buffer, protease, reductive color forming agent Configuration D4
First reagent: buffer, denaturant, protease
Second reagent: buffer, FPDH, reductive color forming agent Configuration D5
First reagent: buffer, denaturant, FPDH, reductive color forming agent
Second reagent: buffer, protease Configuration D6
First reagent: buffer, denaturant, protease, reductive color forming agent
Second reagent: buffer, FPDH Configuration D7
First reagent: buffer, FPDH
Second reagent: buffer, protease, reductive color forming agent Configuration D8
First reagent: buffer, protease
Second reagent: buffer, FPDH, reductive color forming agent Configuration D9
First reagent: buffer, FPDH, reductive color forming agent
Second reagent: buffer, protease Configuration D10
First reagent: buffer, protease, reductive color forming agent
Second reagent: buffer, FPDH Configurations D3 to D10 of Embodiment D may further include the above-described dye stabilizer and/or electron transfer agent.

The buffer, denaturant, reductive color forming agent, and measurement sample in configurations D3 to D10 are the same as those of Embodiment B, and the protease is the same as that of Embodiment C.

[Measurement Apparatus and Measurement System]

In another aspect, the present disclosure relates to an apparatus or system for measuring a glycoprotein in which the measurement method according to the present disclosure is executed.

In one or more embodiments (FIG. 1), the measurement apparatus or measurement system according to the present disclosure includes: a sampling unit 1 for supplying a sample to a reaction vessel (photometric cell); a reagent supply unit 2 for supplying the reagent of a single-reagent system to the reaction vessel (photometric cell); a photometric unit 3 for measuring the developed color signal such as the absorbance in the photometric cell; a control unit 4 for controlling the sampling unit 1, the reagent supply unit 2, and the photometric unit 3; a recording unit 5 for recording photometric data and the like; an arithmetic unit 6 for calculating a glycoprotein level and the like; and a data output unit 7. These units may be included in a single apparatus or may be included in separate apparatuses and form a system.

The glycoprotein level can be measured using HPLC in addition to the measurement method according to the present disclosure. In recent years, the throughput speed of HPLC has been increased. Thus, (only) a single specimen can be measured in about 1 minute, and when a plurality of specimens are measured, the measurement can be performed at a speed of about 5.5 minutes for every 10 specimens (about 30 seconds per specimen).

On the other hand, when a conventional two-reagent system is used in an enzymatic method, the measurement time required for a single specimen is 8 to 10 minutes. However, it is possible to conduct reactions temporally in parallel and to conduct photometry (measurement) at sampling intervals, and therefore, as the number of specimens is increased, the measurement time per specimen can be brought closer to the sampling interval time, and thus the processing time can be made shorter compared with HPLC.

With the measurement method according to the present disclosure, in one or more embodiments, the measurement of a sample can be finished 10 to 180 seconds after the sample and the reagent of a single-reagent system are mixed together, and thus measurement time can be made even shorter compared with a two-reagent system.

Therefore, in one or more embodiments, the apparatus according to the present disclosure can be favorably applied to a large autoanalyzer with which a large number of specimens are processed at a time.

Alternatively, in one or more embodiments, the measurement method according to the present disclosure can also be favorably applied to a small autoanalyzer with which a small number of samples are measured because using the reagent of a single-reagent system makes it possible to reduce the time required for measurement compared with a conventional enzymatic method.

One or more non-limiting embodiments of the apparatus or system according to the present disclosure will be described.

A specimen is supplied to the sampling unit 1 by setting a blood collection tube used to collect blood in the sampling unit as is, transferring blood or the like to a sample cup, or setting a sampling tool in a blood collection tube. When a blood collection tube is set as is, a pierce nozzle that can pass through a cap can also be used.

In the sampling unit 1, a sample is moved to a reaction vessel (photometric cell) from the supplied specimen. The sampling amount is 0.1 to 10 µL, for example. When the sample is moved directly to the photometric cell, the sampling amount is preferably 0.1 to 2 µL from the viewpoint of a dilution ratio. On the other hand, a sample may also be moved to the photometric cell from the specimen via a dilution tank. In this case, the sampling amount is 0.5 to 10 μL, for example.

When the dilution tank is used, erythrocytes in the specimen can be hemolyzed by mixing the specimen with purified water and/or a solution containing a surfactant or the like (also referred to as "hemolyzing solution" hereinafter) in the dilution tank. After hemolysis, the specimen is moved to the photometric cell and used as the measurement sample. Accordingly, the apparatus or system according to the present disclosure may include a hemolyzing solution supply unit for supplying a hemolyzing solution.

On the other hand, the specimen may also be moved directly to the photometric cell. In this case, the specimen may be hemolyzed by supplying the hemolyzing solution or the reagent of a single-reagent system to the photometric cell.

In each case, physical stirring using a stirrer or ultrasonic stirring can be used for hemolysis.

The reagent of a single-reagent system is supplied to the photometric cell from the reagent supply unit 2. In the reagent supply unit 2, a solution of the reagent of a single-reagent system supplied in a single-reagent form may be set, or the reagent of a single-reagent system produced by mixing such amounts of reagents supplied in a two-reagent form (freshly prepared form) that correspond to amounts required for specimens may be set. For example, such an amount of the reagent that is used in a single day or several days or that corresponds to several specimens to several thousands of specimens may be produced.

A sample and the reagent of a single-reagent system may be supplied to the photometric cell in any order or simultaneously. When a whole blood sample is used, a mixing ratio of the sample to the reagent is 1:30 to 2000, for example, preferably 1:100 to 1000, and more preferably 1:150 to 500. When a hemocyte sample is used, a mixing ratio of the sample to the reagent is 1:50 to 4000, for example, preferably 1:100 to 2000, and more preferably 1:250 to 1000.

As noted hereinbefore, the reagent of the single-reagent system may be freshly prepared before use. In a preferred feature, the reagent of a single-reagent system is prepared less than 5 minutes before it is mixed with the sample. This preparation refers to the final step required to bring all components of the reagent together, e.g. the separate reagents described herein. For example, as set out in the examples, the first reagent containing the enzyme may be combined with the second reagent containing the color forming agent to form the reagent of the single-reagent system. The time until the measurement after the sample and the reagent of a single-reagent system are mixed can be set to be in a range of 10 to 180 seconds. The time until the measurement after mixing is 30 seconds or more, 45 seconds or more, or 60 seconds or more, for example. Moreover, the time until the measurement after mixing is 30 seconds or less, 45 seconds or less, 60 seconds or less, 90 seconds or less, 120 seconds or less, or 180 seconds or less, for example.

The measurement is performed by measuring the developed color signal such as absorbance in the photometric cell in the photometric unit 3.

Regarding the measurement of a glycoprotein, the first measurement is performed immediately after the measurement reagent is added, the second measurement is performed at the end of the first measurement, and the difference between the photometric value obtained in the second measurement and the photometric value obtained in the first measurement is taken as the measurement value.

Hemoglobin is measured at a wavelength at which the absorption spectrum of Hb includes absorption, but a wavelength at which the absorption spectrum of Hb is not affected by the color forming reaction of glycohemoglobin is preferable. When DA-67 is used as the color forming agent, for example, the measurement is performed at a wavelength of 550 nm or less, for example, preferably 500 nm or less, and more preferably near 450 to 480 nm.

A measurement cell or hemolysis cell may be washed and reused many times, or may be used only once and then disposed of.

The control unit 4 controls the sampling unit 1, the reagent supply unit 2, the photometric unit 3, and optionally the hemolyzing solution supply unit such that these units work as described above.

Data measured in the photometric unit 3 is recorded in the recording unit 5. In addition, the glycoprotein level and the protein level and/or the glycoprotein ratio are calculated based on the data in the arithmetic unit 6 and recorded in the recording unit 5. The recorded data is output from the data output unit.

The glycoprotein level is obtained by converting the value calculated based on the data (such as the amount of change in the absorbance) based on the calibration curve for the value in the arithmetic unit 6.

The present disclosure may relate to the following one or more non-limiting embodiments.

[1] A method for measuring a glycoprotein in a sample, including (1) to (3) below,
wherein a single reagent is mixed with a sample in order to perform (2) and (3) below:
(1) denaturing a protein in the sample;
(2) reacting a glycoprotein in the sample with amadoriase to allow a color forming agent to produce a color; and
(3) calculating the glycoprotein level by measuring the absorbance of the sample after (1) and (2).

[2] The method for measuring a glycoprotein according to [1], wherein the glycoprotein is glycohemoglobin or glycoalbumin, and the protein is hemoglobin or albumin.

[3] A method for measuring glycohemoglobin in a sample, including (1) to (4) below,
wherein a single reagent is mixed with a sample in order to perform (1) to (4) below:
(1) denaturing hemoglobin in the sample;
(2) reacting glycohemoglobin in the sample with amadoriase to allow a color forming agent to produce a color;
(3) calculating the glycohemoglobin level by measuring the absorbance of the sample after (1) and (2); and
(4) calculating the hemoglobin level by measuring the absorbance of the sample after (1) and (2).

[4] A method for measuring glycohemoglobin in a sample, including (0) to (4) below,
wherein a single reagent is mixed with a sample in order to perform (2) to (4) below:
(0) hemolyzing erythrocytes in the sample to release hemoglobin from the erythrocytes;
(1) denaturing hemoglobin in the sample;
(2) reacting glycohemoglobin in the sample with amadoriase to allow a color forming agent to produce a color;
(3) calculating the glycohemoglobin level by measuring the absorbance of the sample after (1) and (2); and
(4) calculating the hemoglobin level by measuring the absorbance of the sample after (1) and (2).

[5] The measurement method according to any one of [2] to [4], wherein the glycohemoglobin is hemoglobin A1c.

[6] The measurement method according to any one of [1] to [5], wherein the amadoriase is glycoprotein-directed amadoriase.

[7] The measurement method according to any one of [1] to [6], wherein the added reagent contains a denaturant, a glycoprotein-directed fructosyl peptide oxidase, a peroxidase, and an oxidative color forming agent.

[8] The measurement method according to any one of [1] to [6], wherein the added reagent contains a denaturant, a glycoprotein-directed fructosyl peptide dehydrogenase, and a reductive color forming agent.

[9] The measurement method according to any one of [2] to [8], wherein step (2) is a step of reacting glycohemoglobin in the sample with a protease to produce an N-terminal glycated peptide and reacting the N-terminal glycated peptide with amadoriase to allow a color forming agent to produce a color.

[10] The measurement method according to any one of [1] to [5] and [9], wherein the added reagent contains a denaturant, a protease, a fructosyl peptide oxidase, a peroxidase, and a color forming agent.

[11] The measurement method according to any one of [1] to [5] and [9], wherein the added reagent contains a denaturant, a protease, a fructosyl peptide dehydrogenase, and a color forming agent.

[12] An apparatus or system for measuring a glycohemoglobin in which the measurement method according to any one of [1] to [11] is executed.

Hereinafter, the present disclosure will be described more specifically by way of examples, but these examples are merely exemplary, and the present disclosure is not limited to these examples.

EXAMPLES

Example 1

Reagent (a Single-Reagent System)
Glycoprotein-directed fructosyl peptide oxidase 3000 U/L
Myristyldimethylaminopropanesulfonic acid (Tokyo Chemical Industry Co., Ltd.) 3 g/L
POD 10 KU/L
DA-67 (Wako Pure Chemical Corporation) 0.1 mmol/L
MOPS (Dojindo Laboratories) 50 mmol/L
NaOH pH16.5
Measurement Apparatus
BM-6010 (manufactured by JEOL Ltd.)
Operations
2 µL of human whole blood and 148 µL of the reagent of the single-reagent system were mixed and incubated at 37° C. for 2 minutes during which time measurements were taken as set out below.
Measurement of Absorbance
Measurement of glycohemoglobin: The absorbances were measured at a main wavelength of 654 nm and a complementary wavelength of 694 nm about 20 seconds and again about 2 minutes after the reagent was mixed, and the amount of change in the absorbance was determined by subtracting the absorbance after about 20 seconds from the absorbance after about 2 minutes.
Measurement of hemoglobin: The absorbance was measured at a main wavelength of 478 nm and a complementary wavelength of 694 nm about 2 minutes after the reagent was mixed.

Calculation of Glycohemoglobin Level
The glycoprotein level is calculated by converting the amount of change in the absorbance into the glycoprotein level based on the calibration curve for the amount of change in the absorbance.

Example 2

First reagent (containing enzyme) for freshly preparing the single-reagent system reagent
Glycoprotein-directed fructosyl peptide oxidase 400 U/L
POD 20 KU/L
MOPS (Dojindo Laboratories) 50 mmol/L
NaOH pH16.5
Second reagent (containing color forming agent) for freshly preparing single-reagent system reagent
Myristyldimethylaminopropanesulfonic acid (Tokyo Chemical Industry Co., Ltd.) 30 g/L
DA-67 (Wako Pure Chemical Corporation) 1.0 mmol/L
MOPS (Dojindo Laboratories) 50 mmol/L
NaOH pH6.5
Measurement Apparatus
BM-6010 (manufactured by JEOL Ltd.)
Operations
9 mL of the first reagent and 1 mL of the second reagent were mixed together to produce the single-reagent system reagent.
2 µL of human whole blood and 148 µL of the reagent were mixed and incubated at 37° C. for 2 minutes during which time measurements were taken as set out below.
Measurement of Absorbance
Measurement of glycohemoglobin: The absorbances were measured at a main wavelength of 654 nm and a complementary wavelength of 694 nm about 20 seconds and again about 2 minutes after the reagent was mixed, and the amount of change in the absorbance was determined by subtracting the absorbance after about 20 seconds from the absorbance after about 2 minutes.
Measurement of hemoglobin: The absorbance was measured at a main wavelength of 478 nm and a complementary wavelength of 694 nm about 2 minutes after the reagent for the single-reagent system was mixed.
Calculation of Glycohemoglobin Level
The glycoprotein level is calculated by converting the amount of change in the absorbance into the glycoprotein level based on the calibration curve for the amount of change in the absorbance.

Example 3

First reagent (containing enzyme) for freshly preparing the single-reagent system reagent
Fructosyl peptide dehydrogenase 500 U/L
1-Methoxy PMS (Dojindo Laboratories) 1 mmol/L
MOPS (Dojindo Laboratories) 50 mmol/L
NaOH pH6.5
Second reagent (containing color forming agent) for freshly preparing the single-reagent system reagent
Metalloprotease 20000 KU/L
Myristyldimethylaminopropanesulfonic acid (Tokyo Chemical Industry Co., Ltd.) 30 g/L
WST-4 (Dojindo Laboratories) 1 mmol/L
MOPS (Dojindo Laboratories) 50 mmol/L
NaOH pH6.5
Measurement Apparatus
BM-6010 (manufactured by JEOL Ltd.)

23

Operations 9 mL of the first reagent and 1 mL of the second reagent were mixed together to produce the single-reagent system reagent.

2 μL of human whole blood and 148 μL of the reagent were mixed and incubated at 37° C. for 2 minutes during which time measurements were taken as set out below.

Measurement of Absorbance

Measurement of glycohemoglobin: The absorbances were measured at a main wavelength of 694 nm and a complementary wavelength of 805 nm about 20 seconds and again about 2 minutes after the reagent was mixed, and the amount of change in the absorbance was determined by subtracting the absorbance after about 20 seconds from the absorbance after about 2 minutes.

Measurement of hemoglobin: The absorbance was measured at a main wavelength of 478 nm and a complementary wavelength of 694 nm about 2 minutes after the reagent was mixed.

Calculation of Glycohemoglobin Level

The glycoprotein level is calculated by converting the amount of change in the absorbance into the glycoprotein level based on the calibration curve for the amount of change in the absorbance.

Example 4

First reagent (containing enzyme) for freshly preparing the single-reagent system reagent Fructosyl peptide oxidase 500 U/L
POD 20 KU/L
MOPS (Dojindo Laboratories) 50 mmol/L
NaOH pH6.5

Second reagent (containing color forming agent) for freshly preparing the single-reagent system reagent Metalloprotease 30000 KU/L
Myristyldimethylaminopropanesulfonic acid (Tokyo Chemical Industry Co., Ltd.) 30 g/L
DA-67 (Wako Pure Chemical Corporation) 1.0 mmol/L
MOPS (Dojindo Laboratories) 50 mmol/L
NaOH pH6.5

Measurement Apparatus

BM-6010 (manufactured by JEOL Ltd.)

Operations 9 mL of the first reagent and 1 mL of the second reagent were mixed together to produce the single-reagent system reagent.

2 μL of human whole blood and 148 μL of the reagent were mixed and incubated at 37° C. during which time measurements were taken as set out below.

Measurement of Absorbance

Measurement of glycohemoglobin: The absorbances were measured at a main wavelength of 658 nm and a complementary wavelength of 694 nm about 20 seconds, about 1 minute, about 2 minutes, and about 5 minutes after the reagent was mixed, and the amounts of change in the absorbance were determined by subtracting the absorbance after about 20 seconds from the respective absorbances after about 1 minute, about 2 minutes, and about 5 minutes.

Measurement of hemoglobin: The absorbance was measured at a main wavelength of 478 nm and a complementary wavelength of 694 nm about 2 minutes after the reagent was mixed.

Calculation of Glycohemoglobin Level

The glycoprotein level was calculated by converting the amount of change in the absorbance into the glycoprotein level based on the calibration curve for the amount of change in the absorbance.

Results

All the measurement results obtained using the absorbances after about 1 minute, about 2 minutes, and about 5 minutes were the same.

The invention may be embodied in other forms without departing from the spirit or essential characteristics thereof. The embodiments disclosed in this application are to be considered in all respects as illustrative and not limiting. The scope of the invention is indicated by the appended claims rather than by the foregoing description, and all changes which come within the meaning and range of equivalency of the claims are intended to be embraced therein.

The invention claimed is:

1. A method for measuring a glycohemoglobin in a sample, comprising:
   mixing the sample and a single reagent, wherein the mixing comprises denaturing a hemoglobin in the sample and reacting a glycohemoglobin in the sample with amadoriase to allow a color forming agent to produce a color; and
   measuring an absorbance of the sample after the denaturing and mixing, and calculating a glycohemoglobin level,
   wherein the single reagent contains a denaturant, the color forming agent and the amadoriase.

2. A method for measuring glycohemoglobin in a sample, comprising:
   mixing the sample and a single reagent, wherein the mixing comprises denaturing hemoglobin in the sample;
   reacting glycohemoglobin in the sample with amadoriase to allow a color forming agent to produce a color;
   measuring an absorbance of the sample after the denaturing and mixing, and calculating a glycohemoglobin level; and
   measuring an absorbance of the sample after the denaturing and mixing, and calculating a hemoglobin level,
   wherein the single reagent contains a denaturant, the color forming agent and the amadoriase.

3. A method for measuring glycohemoglobin in a sample, comprising:
   hemolyzing erythrocytes in the sample to release hemoglobin from the erythrocytes;
   mixing the sample and a single reagent, wherein the mixing comprises denaturing hemoglobin in the sample, and reacting glycohemoglobin in the sample with amadoriase to allow a color forming agent to produce a color;
   measuring an absorbance of the sample after the denaturing and mixing, and calculating a glycohemoglobin level; and
   measuring an absorbance of the sample after the denaturing and mixing, and calculating a hemoglobin level,
   wherein the single reagent contains a denaturant, the color forming agent and the amadoriase.

4. The method according to claim 1, wherein the glycohemoglobin is hemoglobin A1c.

5. The method according to claim 1, wherein the amadoriase is glycoprotein-directed amadoriase.

6. The method according to claim 1, wherein the amadoriase comprises a glycoprotein-directed fructosyl peptide oxidase, the color forming agent is an oxidative color forming agent, and the single reagent further contains a peroxidase.

7. The method according to claim 1, wherein the amadoriase comprises a glycoprotein-directed fructosyl peptide dehydrogenase, and the color forming agent is a reductive color forming agent.

8. The method according to claim 1, wherein the mixing comprises reacting glycohemoglobin in the sample with a protease to produce an N-terminal glycated peptide and reacting the N-terminal glycated peptide with amadoriase to allow a color forming agent to produce a color.

9. The method according to claim 1, wherein the amadoriase comprises a fructosyl peptide oxidase, and the single reagent further contains a protease, and a peroxidase.

10. The method according to claim 1, wherein the amadoriase comprises a fructosyl peptide dehydrogenase, and the single reagent further contains a protease.

11. An apparatus or system for measuring a glycohemoglobin configured to perform the method according to claim 1.

12. The method according to claim 1, wherein the reagent of a single-reagent system is prepared less than 5 minutes before it is mixed with the sample.

13. The method according to claim 1, wherein the time until measurement after the sample and the reagent of a single-reagent system are mixed is from 10 to 180 seconds.

14. The method according to claim 1, wherein the time until measurement after the sample and the reagent of a single-reagent system are mixed is from 30 seconds or more and 120 seconds or less.

15. The method according to claim 1, wherein the time until measurement after the sample and the reagent of a single-reagent system are mixed is from 45 seconds or more and 90 seconds or less.

16. The method according to claim 1, wherein the time until measurement after the sample and the reagent of a single-reagent system are mixed is from 60 seconds or more and 90 seconds or less.

17. The method according to claim 1, wherein the mixing ratio of the sample to the agent is 1:30 to 2000.

18. The method according to claim 1, wherein the mixing ratio of the sample to the agent is 1:100 to 1000.

19. The method according to claim 1, wherein the mixing ratio of the sample to the agent is 1:150 to 500.

* * * * *